US012193826B2

(12) United States Patent
Jiang et al.

(10) Patent No.: US 12,193,826 B2
(45) Date of Patent: Jan. 14, 2025

(54) METHOD, APPARATUS AND ELECTRONIC DEVICE FOR PROCESSING TIME SERIES DATA

(71) Applicants: BOE TECHNOLOGY GROUP CO., LTD., Beijing (CN); Peking University, Beijing (CN)

(72) Inventors: Li Jiang, Beijing (CN); Yongyue Sun, Beijing (CN); Siyang Liang, Beijing (CN); Meng Wu, Beijing (CN); Yude Li, Beijing (CN); Hongyan Li, Beijing (CN); Litong Han, Beijing (CN)

(73) Assignees: BOE TECHNOLOGY GROUP CO., LTD., Beijing (CN); PEKING UNIVERSITY, Beijing (CN)

( * ) Notice: Subject to any disclaimer, the term of this patent is extended or adjusted under 35 U.S.C. 154(b) by 548 days.

(21) Appl. No.: 17/605,278

(22) PCT Filed: Sep. 28, 2020

(86) PCT No.: PCT/CN2020/118489
§ 371 (c)(1),
(2) Date: Oct. 21, 2021

(87) PCT Pub. No.: WO2021/058007
PCT Pub. Date: Apr. 1, 2021

(65) Prior Publication Data
US 2022/0218261 A1    Jul. 14, 2022

(30) Foreign Application Priority Data
Sep. 29, 2019    (CN) .......................... 201910936511.7

(51) Int. Cl.
*G06F 16/23*    (2019.01)
*A61B 5/35*    (2021.01)
(Continued)

(52) U.S. Cl.
CPC ................ *A61B 5/35* (2021.01); *A61B 5/364* (2021.01); *A61B 5/366* (2021.01); *G06F 16/2379* (2019.01)

(58) Field of Classification Search
None
See application file for complete search history.

(56) References Cited

U.S. PATENT DOCUMENTS

| 5,715,829 A | 2/1998 | Arand et al. |
| 5,817,027 A | 10/1998 | Arand et al. |

(Continued)

FOREIGN PATENT DOCUMENTS

| CN | 103729528 A | 4/2014 |
| CN | 103853749 A | 6/2014 |

(Continued)

OTHER PUBLICATIONS

"The Split-Apply-Combine Strategy for Data Analysis" by Hadley Wickham; Journal of Statistical Software; 2011; pp. 1-28.*

(Continued)

*Primary Examiner* — Albert M Phillips, III
*Assistant Examiner* — Jermaine A Mincey
(74) *Attorney, Agent, or Firm* — IP & T GROUP LLP

(57) ABSTRACT

A method for processing time series data comprises: dividing time series data into a plurality of data fragments according to an objective function, the plurality of data fragments having a greatest similarity; in response to determining that at least one data fragment does not satisfy an iteration termination condition, performing following iteration operations on the at least one data fragment; and constructing a time series base pattern library by using a plurality of time series base patterns. The iteration operations includes: using the at least one data fragment as at least one update time series fragment; dividing each update time (Continued)

series fragment into a plurality of update data fragments; using each update data fragment that does not satisfy the iteration termination condition as a new update time series fragment; and using each update data fragment that satisfies the iteration termination condition as a time series base pattern.

20 Claims, 9 Drawing Sheets

(51) Int. Cl.
*A61B 5/364* (2021.01)
*A61B 5/366* (2021.01)

(56) References Cited

U.S. PATENT DOCUMENTS

2016/0246829 A1* 8/2016 Chen ................ G06F 16/22
2019/0034810 A1   1/2019 Zhang

FOREIGN PATENT DOCUMENTS

| CN | 104714953 | A | 6/2015 |
| CN | 107480135 | A | 12/2017 |
| CN | 108680181 | A | 10/2018 |
| CN | 109620210 | A | 4/2019 |
| CN | 109800217 | A | 5/2019 |
| CN | 110188180 | A | 8/2019 |
| CN | 110688414 | A | 1/2020 |
| EP | 3248648 | A1 | 11/2017 |

OTHER PUBLICATIONS

Gary Weiss; Mining with Rarity: A Unifying Framework; ACM; pp. 1-19 (Year: 2004).*

The First Office Action of Priority Application No. CN 201910936511.7 issued by the Chinese Patent Office on Nov. 15, 2021.

* cited by examiner

METHOD, APPARATUS AND ELECTRONIC DEVICE FOR PROCESSING TIME SERIES DATA

CROSS-REFERENCE TO RELATED APPLICATIONS

This application is a national phase entry under 35 USC 371 of International Patent Application No. PCT/CN2020/118489 filed on Sep. 28, 2020, which claims priority to Chinese Application No. 201910936511.7, filed on Sep. 29, 2019, which are incorporated herein by reference in their entirety.

TECHNICAL FIELD

The present disclosure relates to a method, an apparatus and an electronic device for processing time series data, and a non-transitory computer-readable storage medium.

BACKGROUND

Time series data refer to data series recorded in a chronological order. Typical time series data include electrocardiogram (ECG) data, respiration detection data, population change data, economic change data, etc. The time series data generally need to be analyzed to determine statistical characteristics and variation regularity of the data during a period of time. For example, analysis of a patient's ECG data can help doctors determine a health condition of the patient's heart.

In order to determine the statistical characteristics and the variation regularity of the time series data, a specific time series fragment needs to be identified in the time series data. For example, a specific time series fragment in the ECG data may be data at the time of cardiac contraction (also referred to as heartbeat). At present, since the time series data may be continuous in value, complex in noise component, and highly skewed in data, it is still difficult to segment such time series data and identify a specific time series fragment therein.

SUMMARY

In an aspect, a method for processing time series data is provided. The method includes: dividing time series data into a plurality of data fragments according to an objective function, wherein the plurality of data fragments have a greatest similarity; in response to determining that at least one data fragment in the plurality of data fragments does not satisfy an iteration termination condition, performing following iterative operations on the at least one data fragment; and constructing a time series base pattern library by using a plurality of time series base patterns such that the time series base pattern library includes the plurality of time series base patterns. The iterative operations include: using the at least one data fragment as at least one update time series fragment; dividing each update time series fragment into a plurality of update data fragments according to the objective function; using each update data fragment that does not satisfy the iteration termination condition in the plurality of update data fragments as a new update time series fragment, so as to continue to divide the new update time series fragment according to the objective function; and using each update data fragment that satisfies the iteration termination condition in the plurality of update data fragments as a time series base pattern; and constructing the time series base pattern library by using the plurality of time series base patterns such that the time series base pattern library includes the plurality of time series base patterns.

In some embodiments, before constructing the time series base pattern library, the method further includes: using any one of the plurality of data fragments that satisfies the iteration termination condition as another time series base pattern.

In some embodiments, the iteration termination condition is a duration threshold condition.

In some embodiments, constructing the time series base pattern library by using the plurality of time series base patterns, includes: as for each time series base pattern, determining whether a same time series base pattern exists in the time series base pattern library; discarding the time series base pattern in response to determining that the same time series base pattern exists in the time series base pattern library; adding the time series base pattern to the time series base pattern library in response to determining that the same time series base pattern does not exists in the time series base pattern library.

In some embodiments, constructing the time series base pattern library by using the plurality of time series base patterns, includes: adding the plurality of time series base patterns to the time series base pattern library; and deleting a repeated time series base pattern in the time series base pattern library.

In some embodiments, the method further includes: sequencing time series base patterns with different durations in the time series base pattern library according to durations of the time series base patterns; and sequencing time series base patterns with a same duration in the time series base pattern library according to values of the time series base patterns.

In some embodiments, the method further includes: selecting a first time series base pattern and a second time series base pattern from the time series base pattern library, wherein a duration of the first time series base pattern is less than a duration of the second time series base pattern; obtaining a target base pattern fragment from the second time series base pattern; determining whether a similarity between the target base pattern fragment and the first time series base pattern is greater than or equal to a first similarity threshold; updating the second time series base pattern to the target base pattern fragment in response to determining that the similarity between the target base pattern fragment and the first time series base pattern is greater than or equal to the first similarity threshold; and not updating the second time series base pattern in response to determining that the similarity between the target base pattern fragment and the first time series base pattern is less than the first similarity threshold.

In some embodiments, the method further includes: deleting a repeated time series base pattern in the time series base pattern library.

In some embodiments, the method further includes: adding a base pattern identifier to each time series base pattern in the time series base pattern library.

In some embodiments, the method further includes: obtaining time series data to be identified; dividing the time series data to be identified into a plurality of data fragments to be identified according to time series base patterns in the time series base pattern library; and as for at least one of the plurality of data fragments to be identified, converting each data fragment to be identified into the base pattern identifier of a corresponding time series base pattern, wherein a similarity between the data fragment to be identified and the corresponding time series base pattern is greater than or equal to a second similarity threshold.

In some embodiments, dividing the time series data to be identified into the plurality of data fragments to be identified according to the time series base patterns in the time series base pattern library, includes: selecting at least one time series base pattern in the time series base pattern library according to a duration sequence of the time series base patterns and/or a value sequence of the time series base patterns; and dividing the time series data to be identified into the data fragments to be identified according to the at least one selected time series base pattern.

In some embodiments, dividing the time series data to be identified into the data fragments to be identified according to the at least one selected time series base pattern, includes: dividing the time series data to be identified into at least one data fragment to be identified according to a selected time series base pattern; determining whether a similarity between any one of the at least one data fragment to be identified and the selected time series base pattern is less than the second similarity threshold; and selecting a next time series base pattern in the time series base pattern library to divide remaining time series data to be identified according to the duration sequence of the time series base patterns and/or the value sequence of the time series base patterns, in response to determining that the similarity between any one of the at least one data fragment to be identified and the selected time series base pattern is less than the second similarity threshold. Converting the each data fragment to be identified into the base pattern identifier of the corresponding time series base pattern, includes: converting the data fragment to be identified into a base pattern identifier corresponding to the selected time series base pattern, in response to determining that the similarity between any one of the at least one data fragment to be identified and the selected time series base pattern is greater than or equal to the second similarity threshold.

In some embodiments, dividing the time series data to be identified into the data fragments to be identified according to the at least one selected time series base pattern further includes: discarding a first frame of data in the time series data to be identified if the similarity between any data fragment to be identified and a corresponding time series base pattern is less than the second similarity threshold when the time series data to be identified are divided into at least one data fragment to be identified according to any time series base pattern in the time series base pattern library; and using remaining data of the time series data to be identified as new time series data to be identified.

In some embodiments, the method further includes: converting the time series data to be identified into a base pattern identifier series, the base pattern identifier series being composed of at least one base pattern identifier corresponding to the at least one data fragment to be identified; identifying a base pattern identifier combination from the base pattern identifier series; determining whether an identification result satisfies a preset condition; updating the time series data to be identified by using one or more hyper-parameters in response to determining that the identification result satisfies the preset condition; and not updating the time series data to be identified in response to determining that the identification result does not satisfy the preset condition.

In some embodiments, the similarity is calculated by a similarity function, and the similarity function is any one of following functions: cosine similarity calculation function, Euclidean distance calculation function, Manhattan distance calculation function, Minkowski distance calculation function or Pearson correlation coefficient calculation function.

In another aspect, an apparatus for processing time series data is provided. The apparatus includes an initialization circuit, an iterative circuit and an output circuit. The initialization circuit is configured to divide time series data into a plurality of data fragments according to an objective function, the objective function enables the plurality of data fragments to have a greatest similarity. The iterative circuit is configured to perform iterative operations on at least one data fragment in response to determining that the at least one data fragment in the plurality of data fragments does not satisfy an iteration termination condition; the iterative operations includes: using the at least one data fragment as at least one update time series fragment; dividing each update time series fragment into a plurality of update data fragments according to the objective function; using each update data fragment that does not satisfy the iteration termination condition in the plurality of update data fragments as a new update time series fragment, so as to continue to divide the new update time series fragment according to the objective function; and using each update data fragment that satisfies the iteration termination condition in the plurality of update data fragments as a time series base pattern. The output circuit is configured to construct a time series base pattern library by using a plurality of time series base patterns such that the time series base pattern library includes the plurality of time series base patterns.

In some embodiments, the apparatus further includes a denoising circuit configured to perform following denoising operations: selecting a first time series base pattern and a second time series base pattern from the time series base pattern library, wherein a duration of the first time series base pattern is less than a duration of the second time series base pattern; obtaining a target base pattern fragment from the second time series base pattern; determining whether a similarity between the target base pattern fragment and the first time series base pattern is greater than or equal to a first similarity threshold; updating the second time series base pattern to the target base pattern fragment in response to determining that the similarity between the target base pattern fragment and the first time series base pattern is greater than or equal to the first similarity threshold; and not updating the second time series base pattern in response to determining that the similarity between the target base pattern fragment and the first time series base pattern is less than the first similarity threshold.

In some embodiments, the apparatus further includes an identification circuit configured to add a base pattern identifier to each time series base pattern in the time series base pattern library.

In yet another aspect, an electronic device for processing time series data is provided, and the electronic device includes a processor and a memory. The memory has stored therein computer instructions that, when executed by the processor, cause the processor to implement the method for processing the time series data.

In yet another aspect, a non-transitory computer-readable storage medium is provided. The computer-readable storage medium has stored thereon computer program instructions that, when executed by a processor, cause the processor to perform one or more steps of the method for processing the time series data as described in any of the above embodiments.

In yet another aspect, a computer program product is provided. The computer program product includes computer program instructions that, when executed on a computer, cause the computer to execute one or more steps in the method for processing the time series data as described in any of the above embodiments.

In yet another aspect, a computer program is provided. When executed on a computer, the computer program causes the computer to execute one or more steps in the method for processing the time series data as described in any of the above embodiments.

BRIEF DESCRIPTION OF THE DRAWINGS

In order to describe technical solutions in the present disclosure more clearly, accompanying drawings to be used in some embodiments of the present disclosure will be introduced briefly below. Obviously, the accompanying drawings to be described below are merely accompanying drawings of some embodiments of the present disclosure, and a person of ordinary skill in the art may obtain other drawings according to these drawings. In addition, the accompanying drawings to be described below may be regarded as schematic diagrams, and are not limitations on actual sizes of products, actual processes of methods and actual timings of signals involved in the embodiments of the present disclosure.

DETAILED DESCRIPTION

Figure 1:
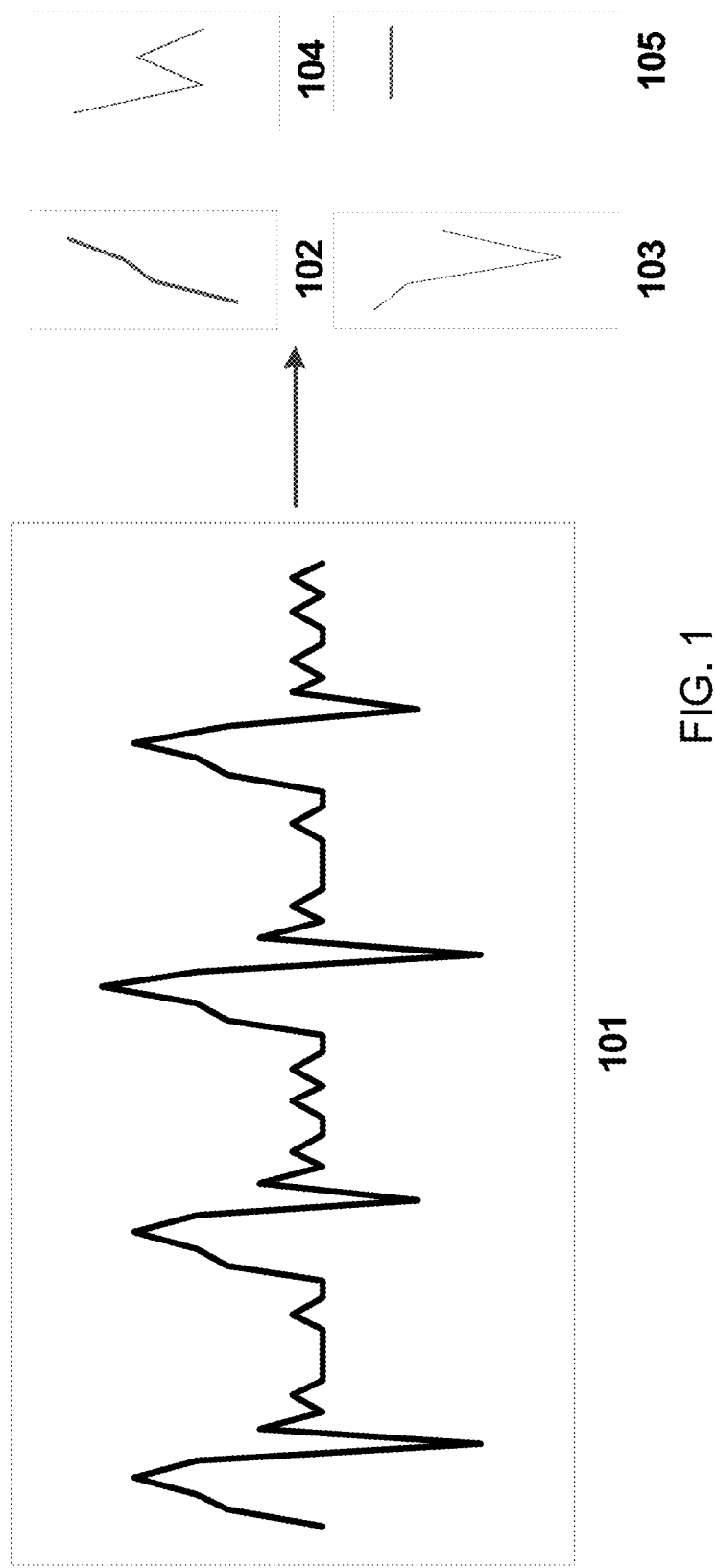
FIG. 1 is a time series data analysis diagram of a method for processing time series data, in accordance with some embodiments.

Technical solutions in some embodiments of the present disclosure will be described clearly and completely below with reference to the accompanying drawings. Obviously, the described embodiments are merely some but not all embodiments of the present disclosure. All other embodiments obtained by a person of ordinary skill in the art based on the embodiments of the present disclosure shall be included in the protection scope of the present disclosure.

Unless the context requires otherwise, throughout the description and the claims, the term "comprise" and other forms thereof such as the third-person singular form "comprises" and the present participle form "comprising" are construed as open and inclusive meaning, i.e., "including, but not limited to." In the description of the specification, the terms such as "one embodiment", "some embodiments", "exemplary embodiments", "example", "specific example" or "some examples" are intended to indicate that specific features, structures, materials or characteristics related to the embodiment(s) or example(s) are included in at least one embodiment or example of the present disclosure. Schematic representations of the above terms do not necessarily refer to the same embodiment(s) or example(s). In addition, the specific features, structures, materials, or characteristics may be included in any one or more embodiments or examples in any suitable manner.

Hereinafter, the terms such as "first" and "second" are used for descriptive purposes only, and are not to be construed as indicating or implying the relative importance or implicitly indicating the number of indicated technical features. Thus, a feature defined by "first" or "second" may explicitly or implicitly includes one or more of the features. In the description of the embodiments of the present disclosure, the term "a plurality of" or "the plurality of" means two or more unless otherwise specified.

The phrase "A and/or B" includes the following three combinations: only A, only B, and a combination of A and B.

As used herein, the term "if" is optionally construed as "when" or "in a case where" or "in response to determining that" or "in response to detecting that", depending on the context. Similarly, the phrase "if it is determined that" or "if [a stated condition or event] is detected" is optionally construed as "in a case where it is determined that" or "in response to determining that" or "in a case where [the stated condition or event] is detected" or "in response to detecting [the stated condition or event]", depending on the context.

The use of the phrase "configured to" herein indicates an open and inclusive expression, which does not exclude devices that are configured to perform additional tasks or steps.

In addition, the use of the phrase "based on" indicates openness and inclusiveness, since a process, step, calculation or any other action that is "based on" one or more of the stated conditions or values may be based on additional conditions or values exceeding those stated in practice.

Referring to FIG. 1, time series data 101 are processed by using a method for processing time series data to extract specific time series fragments 102, 103, 104 and 105. The time series data may be any data series recorded in a chronological order, such as electrocardiogram (ECG) data, respiration detection data, population change data, economic change data, etc. Durations of the specific time series fragments 102, 103, 104 and 105 may be the same or different. A combination of these specific time series fragments may be used to characterize statistical characteristics and variation regularity of the time series data. For example, in the time series data 101 in FIG. 1, the specific time series fragments always appear repeatedly in the combination of the time series fragments 102, 103, 104 and 105.

The time series data contain noise and have a characteristic of data skew. The data skew refers to a situation where specific data is non-uniformly distributed throughout the time series data. Taking ECG data as an example, the ECG data contain noise. The ECG data are generally ECG signals that are continuously acquired, and the acquired ECG signals are generally weak and inevitably include various noises, such as power-line interference, electrode contact noise, human movement, electromyographic interference, baseline drift, ECG amplitude variation during breathing, or equipment and instrument noise. In addition, as for cardiac patients, useful data are data at a moment of arrhythmia. However, since arrhythmia is not frequently and chronically attack, for example, some paroxysmal arrhythmias (such as paroxysmal supraventricular tachycardia) have a continuous attack time of less than 30 seconds and are difficult to capture, most of the ECG data are of normal rhythms, and the ECG data have natural data high skewness. In order to process such time series data, methods including a threshold-based method, a wavelet transform method, a principal component analysis (abbreviated as PCA) method, and a composite model-based method have been proposed.

The threshold-based method uses a threshold-based digital filter to attenuate noise in the time series data and eliminate fluctuating baselines. The threshold-based digital filter includes a savitsky-golay smoothing filter (SGSF), a high-pass filter, a differentiator, etc. The wavelet transform method is based on multi-resolution wavelets to identify the specific time series fragments 102, 103, 104 and 105. The wavelet transform method uses characteristics of a basic wavelet of the time series data to identify the time series fragments. However, in the wavelet transform method, once the basic wavelet is determined, all signal analyses will be performed by using the basic wavelet, which makes the wavelet transform method not widely applicable to different kinds of time series data. The PCA method linearly converts the time series data into a new coordinate system, and may perform a pattern identification and a dimensionality reduction while retaining information data. The composite model-based method combines a hidden markov model (HMM) with a threshold, which are applied to an identification of specific time series fragments.

However, hyper-parameters of the model in the method for processing the time series data are fixed, and a processing effect on the time series data mainly depends on selection of the hyper-parameters. Therefore, these methods may not be adaptively applied to processing of different kinds of time series data. Besides, these methods are mainly applied to uniformly distributed data and are difficult to adaptively deal with noise disturbance. Thus, as for time series data with highly complex noise and severe data skew (such as the ECG data), these methods cannot achieve ideal results.

Some embodiments of the present disclosure provide a method for processing time series data. The method for processing the time series data automatically extracts time series base patterns of the time series data, constructs a time series base pattern library accordingly, and then utilizes the time series base pattern library to identify specific time series fragments of time series data to be identified. The method for processing the time series data in the embodiments of the present disclosure may significantly improve an effect on analyzing and processing the time series data, especially may identify specific time series fragments in time series data with continuous values, complex noise components and severe data skew.

The method for processing the time series data in the embodiments of the present disclosure may be applied to any electronic device, such as a smart phone, a tablet computer, a desktop computer, a multi-core computer, a server. The method for processing the time series data may also be executed by a central processing unit or an image processor of the electronic device in cooperation with corresponding computer program codes.

The method for processing the time series data includes S201 to S203. An execution body of the method for processing the time series data may be a processor, or may be other devices or apparatuses.

In S201, the time series data are divided into a plurality of data fragments according to an objective function, and the plurality of data fragments have a greatest similarity.

In some examples, the time series data include a plurality of frames of data, and each frame of data represents a sample value at a certain point in time. Each data fragment includes multiple consecutive frames of data in the time series data.

The objective function may adopt a variety of manners to achieve a division of the time series data. In some examples, the objective function determines which division manner may enable the plurality of data fragments to have the greatest similarity by pairwise comparing the similarities between the data fragments divided according to different division manners. It is assumed that the time series data include 1000 frames of data, and the time series data are to be divided into 2 data fragments. The objective function divides the time series data in a variety of division manners. For example, the objective function adopts a first division manner to divide the time series data into two data fragments in which first 300 frames of data are a data fragment and last 700 frames of data are another data fragment, and the objective function adopts a second division manner to divide the time series data into two data fragments in which first 500 frames of data are a data fragment and last 500 frames of data are another data fragment. In this case, the objective function calculates the similarity between data fragments obtained by each division manner. That is, the objective function calculates the similarity between the data fragment of the first 300 frames of data and the data fragment of the last 700 frames of data, and the similarity between the data fragment of the first 500 frames of data and the data fragment of the last 500 frames of data. After calculating the similarities between the data fragments in all the division manners, the objective function obtains a division manner that may enable the data fragments to have the greatest similarity, for example, by sequencing, so as to obtain the plurality of data fragments corresponding to the division manner.

Of course, the objective function may also divide the time series data into the plurality of data fragments with a maximum similarity in other ways. The embodiments of the present disclosure do not limit a specific implementation of the objective function, as long as the plurality of data fragments with the maximum similarity can be obtained.

Figure 2A:
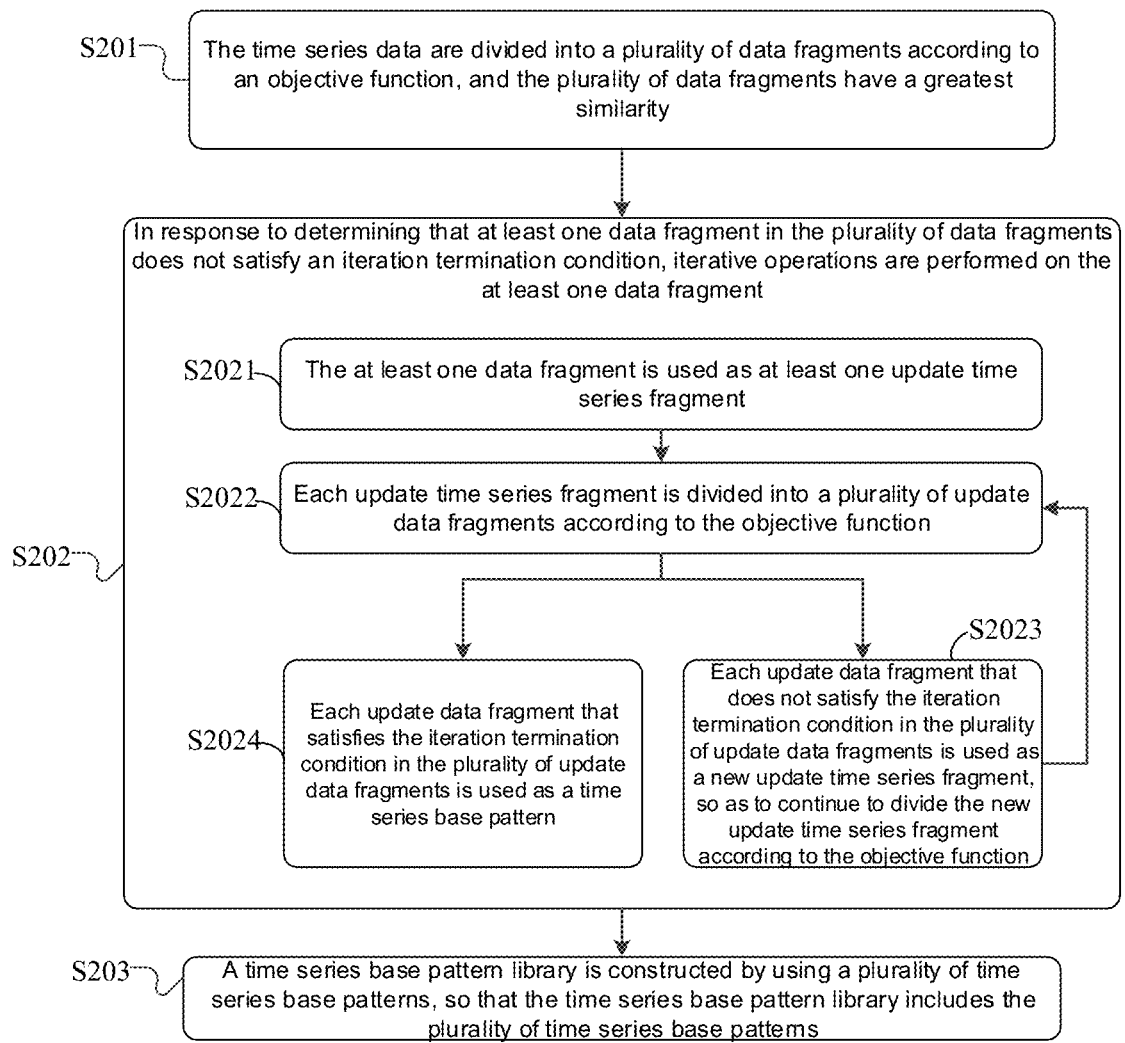
FIG. 2A is a flow diagram of a method for processing time series data, in accordance with some embodiments.
Figure 2B:
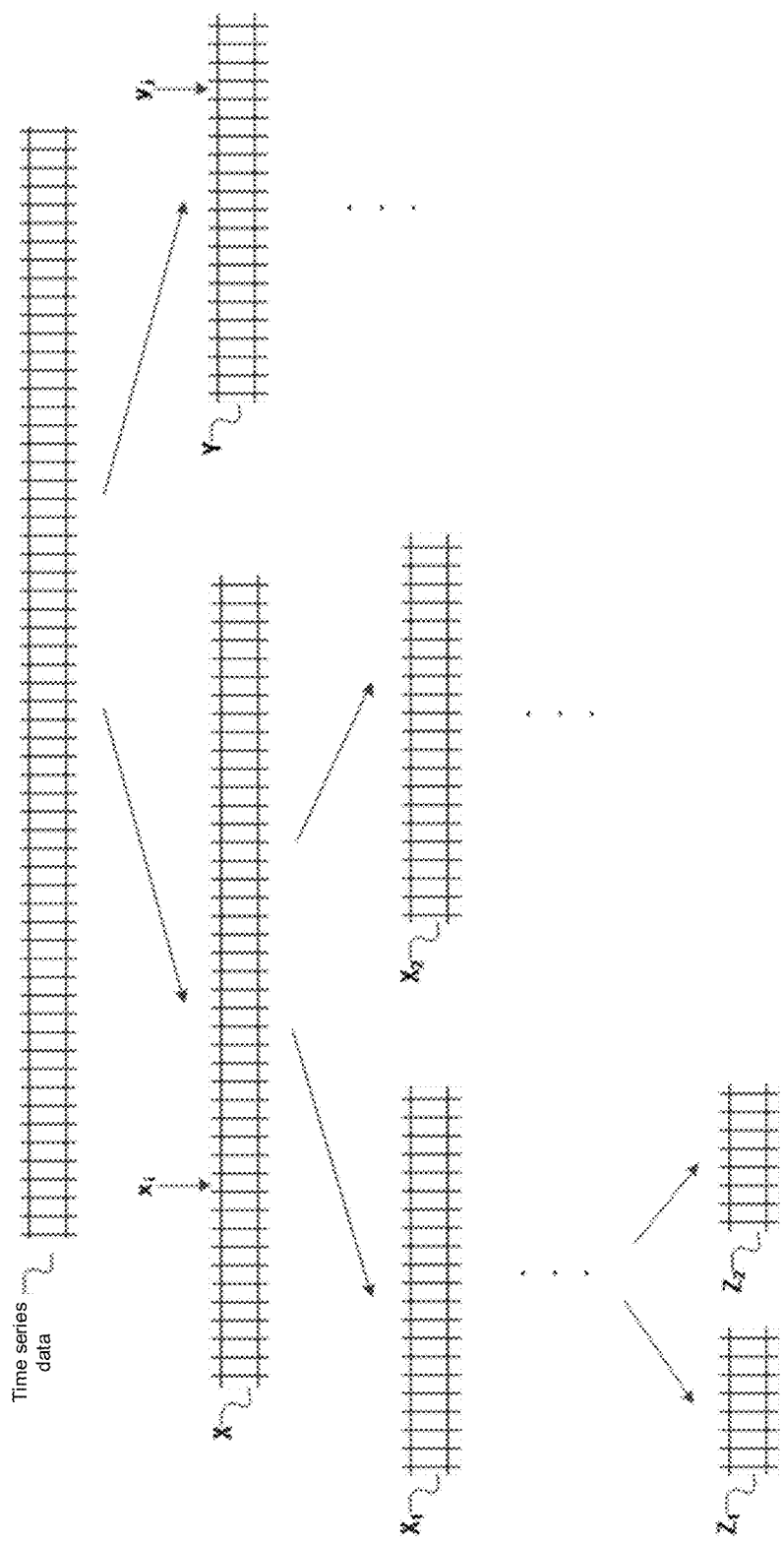
FIG. 2B is a structural diagram showing a process of a method for processing time series data, in accordance with some embodiments.

It will be noted that the above description is made by taking an example in which the objective function divides the time series data into two data fragments. In some embodiments of the present disclosure, the objective function may also divide the time series data into three or more data fragments. The embodiments of present disclosure do not limit the number of data fragments. The more data fragments the time series data are divided into, the more computing resources the objective function needs. Therefore, the number of data fragments may be determined according to the computing resources of the electronic device. In some examples, in order to improve a computational efficiency, the objective function divides the time series data into two or three data fragments in each iteration. Referring to FIG. 2B, the objective function divides the time series data into two data fragments $X\{x_i\}$ and $Y\{y_j\}$, where $x_i$ and $y_j$ represent any frame of data in the data fragments X and Y, respectively.

Optionally, the data fragments divided by the objective function need to satisfy a certain condition to ensure readability of the data fragments.

In an example in which the time series data are the ECG data, as for the ECG data, each heartbeat may be divided into a P wave, a Q wave, an R wave, an S wave and a T wave. The most significant for a heartbeat is a QRS complex composed of the Q wave, the R wave and the S wave. For an adult, the QRS complex generally lasts for 0.06 s to 0.1 s, whereas for a young child, a duration of the QRS complex is generally shorter. Therefore, a corresponding duration threshold may be set to ensure an effective identification of the Q wave, the R wave and the S wave of the QRS complex in the heartbeat. For example, the duration threshold of the data fragments into which the ECG data is divided is greater than or equal to 20 ms and less than or equal to 60 ms. For example, the duration threshold is set to 20 ms, 50 ms or 60 ms. As for other time series data, the duration threshold of the data fragments may also be set in a similar manner. For example, as for stock data, the duration threshold may be set to not less than 1 hour.

It will be noted that the embodiments of the present disclosure are not limited to only setting the duration threshold to make the data fragments readable, and other conditions, or both the duration threshold and other conditions may be used to make the data fragments readable.

In some embodiments, the objective function calculates the similarity between the data fragments through a similarity function. In some examples, the similarity function is any one of the following functions: cosine similarity calculation function, Euclidean distance calculation function, Manhattan distance calculation function, Minkowski distance calculation function or Pearson correlation coefficient calculation function. The similarity may also be an average value of the similarities calculated by a plurality of similarity functions in the aforementioned functions.

The above similarity functions are described by taking an example in which the time series data are divided into two data fragments. The cosine similarity calculation function takes each data fragment as a vector in a vector space and calculates a cosine value of an included angle between two vectors. The closer the cosine value is to 1, the more similar the two data fragments are. The Euclidean distance calculation function calculates a Euclidean distance between two data fragments, and uses the Euclidean distance as a measure standard of the similarity between the data fragments. The Manhattan distance calculation function calculates a Manhattan distance between two data fragments and use the Manhattan distance as a measure standard of the similarity between the data fragments. The Minkowski distance calculation function calculates a Minkowski distance between two data fragments and uses the Minkowski distance as a measure standard of the similarity between the data fragments.

In S202, in response to determining that at least one data fragment in the plurality of data fragments does not satisfy an iteration termination condition, iterative operations are performed on the at least one data fragment. The iterative operations include S2021 to S2024.

In S2021, the at least one data fragment is used as at least one update time series fragment.

In S2022, each update time series fragment is divided into a plurality of update data fragments according to the objective function.

For example, referring to FIG. 2B, it is assumed that the time series data are divided into two data fragments X and Y in the S201. If it is determined that the data fragment X has satisfied the iteration termination condition, the iterative operations may not be performed on the data fragment X. If it is determined that the data fragment Y has satisfied the iteration termination condition, the iterative operations may not be performed on the data fragment Y. If it is determined that neither the data fragment X nor the data fragment Y satisfies the iteration termination condition, the data fragment X is regarded as an update time series fragment and the data fragment Y is regarded as another update time series fragment in the S2021. And the two update time series fragments are further divided in S2022.

In the S2022, the update time series fragment is divided by using the objective function in the S201. For example, referring to FIG. 2B, by using the objective function, the data fragment X may continue to be divided into two updated data fragments $X_1$ and $X_2$ with the maximum similarity, and the data fragment Y may continue to be divided into two updated data fragments $Y_1$ and $Y_2$ with the maximum similarity or three update data fragments $Y_1$, $Y_2$, and $Y_3$, with the maximum similarity.

In S2023, each update data fragment that does not satisfy the iteration termination condition in the plurality of update data fragments is used as a new update time series fragment, so as to continue to divide the new update time series fragment according to the objective function.

In S2024, each update data fragment that satisfies the iteration termination condition in the plurality of update data fragments is used as a time series base pattern.

In addition, if a data fragment that satisfies the iteration termination condition exists among the plurality of data fragments, the data fragment is directly used as another time series base pattern.

The iteration termination condition may be various, and may be different according to characteristics of the time series data. The embodiments of the present disclosure do not limit the setting of the iteration termination condition, as long as the obtained time series base pattern library can meet analysis requirements of the time series data. In some examples, the iteration termination condition is a duration threshold condition. In an example in which the time series data are the ECG data, in FIG. 2B, updated data fragments $Z_1$ and $Z_2$ are obtained during a certain iteration. It is assumed that $Z_1$ satisfies the iteration termination condition (for example, a duration of $Z_1$ has satisfied the duration threshold condition), $Z_1$ is used as a time series base pattern. And it is assumed that $Z_2$ does not satisfy the iteration termination condition (for example, a duration of $Z_2$ still does not satisfy the duration threshold condition), $Z_2$ needs to be used as a new update time series fragment, and the new update time series fragment is further divided according to the objective function until the iteration termination condition is satisfied.

In S203, a time series base pattern library is constructed by using a plurality of time series base patterns, so that the time series base pattern library includes the plurality of time series base patterns.

For example, in FIG. 2B, $Z_1$ has satisfied the iteration termination condition, and $Z_1$ is added to the time series base pattern library.

After S201 to S203, the plurality of time series base patterns from the time series data are determined and stored in the time series base pattern library. These time series base patterns may be used to identify the time series data to be identified that have similar characteristics to the time series data.

Optionally, the time series base patterns in the time series base pattern library are not repeated.

In a case where the time series base pattern is not selected, there may be a repeated time series base pattern in the time series base pattern library constructed by all the time series base patterns from the time series data. Therefore, various manners may be used to ensure uniqueness of the time series base patterns when the time series base pattern library is constructed.

In some examples, as for each time series base pattern, before it is added to the time series base pattern library, it is first determined whether a same time series base pattern exists in the time series base pattern library. In response to determining that the same time series base pattern exists in the time series base pattern library, the time series base pattern is discarded. In response to determining that no same time series base pattern exists in the time series base pattern library, the time series base pattern is added to the time series base pattern library. For example, if it is determined that a time series base pattern that is the same as the time series base pattern $Z_1$ has existed in the time series base pattern library, the time series base pattern $Z_1$ is not added to the time series base pattern library, but $Z_1$ is directly discarded. Herein, as for a first time series base pattern to be added to the time series base pattern library, there is no need to determine whether a same time series base pattern exists in the time series base pattern library.

In some other examples, the plurality of time series base patterns are added to the time series base pattern library, and then a repeated time series base pattern in the time series base pattern library is deleted.

That is, all the obtained time series base patterns are added to the time series base pattern library without any selection, and then the repeated time series base pattern is deleted.

Optionally, the method for processing the time series data further includes: adding a base pattern identifier to each time series base pattern in the time series base pattern library. For example, as for the ECG data, a P wave identifier is added to a time series base pattern whose waveform is similar to the P wave. Similarly, any of Q wave identifier, R wave identifier, S wave identifier or T wave identifier may be added to other time series base patterns.

The time series base pattern library may be used for identification of the same type of data as the time series data. For example, it is assumed that the ECG data of a patient with arrhythmia are used to construct a time series base pattern library for detecting a specific time series fragment of the arrhythmia, and such a time series base pattern library may be used to identify the ECG data of other patients with arrhythmia.

The method for processing the time series data in the embodiments of the present disclosure may directly use any time series data to construct a base pattern library of that type of time series data, without constructing a model with fixed hyper-parameters. Compared with a common method for processing the time series data, the method for processing the time series data in the embodiments of the present disclosure has higher adaptability and robustness, and may be adaptively applied to process various types of time series data. The plurality of time series base patterns in the method for processing the time series data in the embodiments of the present disclosure may correspond to a same base pattern identifier. Therefore, as for a specific time series fragment, the embodiments of the present disclosure adaptively construct a plurality of time series base patterns that may be used to identify the specific time series fragment, which may accurately and comprehensively identify similar specific time series fragments in the time series data to be identified that are similar to the time series data.

Figure 3A:
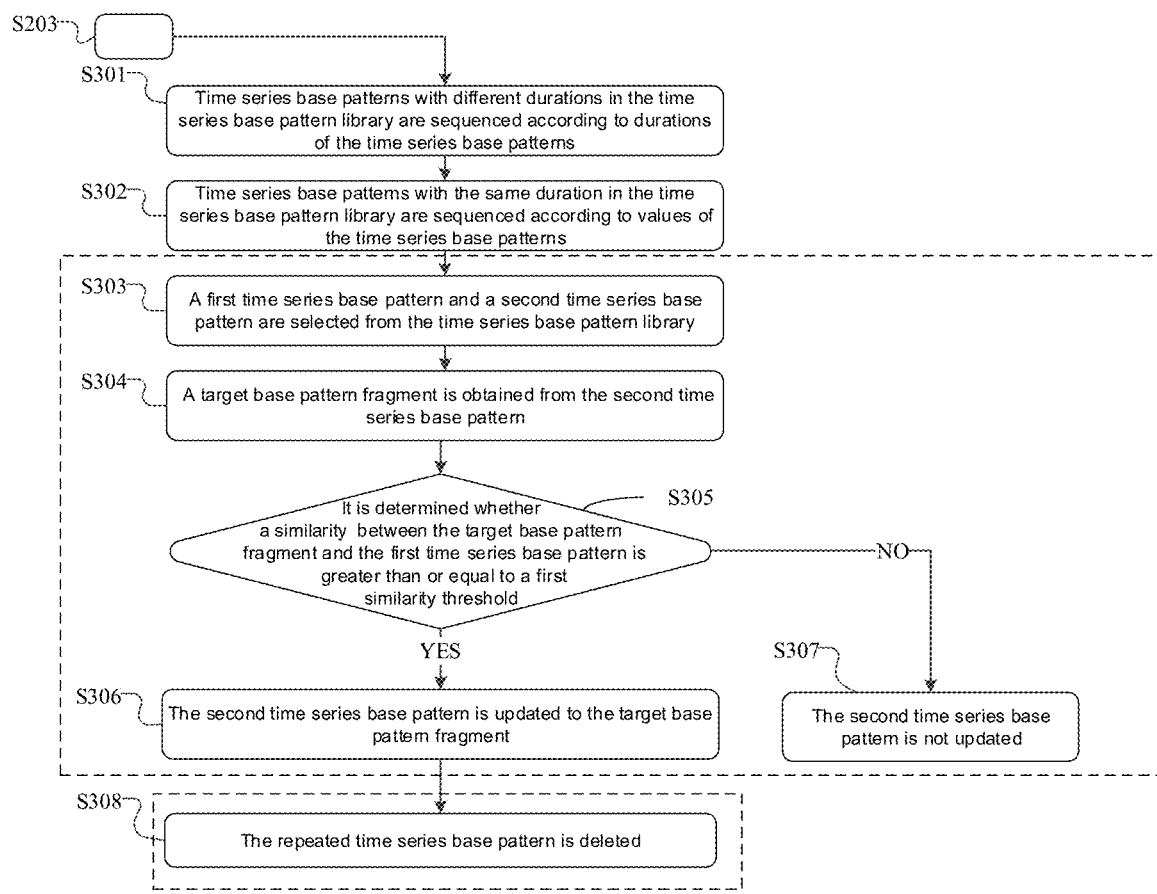
FIG. 3A is a flow diagram of another method for processing time series data, in accordance with some embodiments.
Figure 3B:
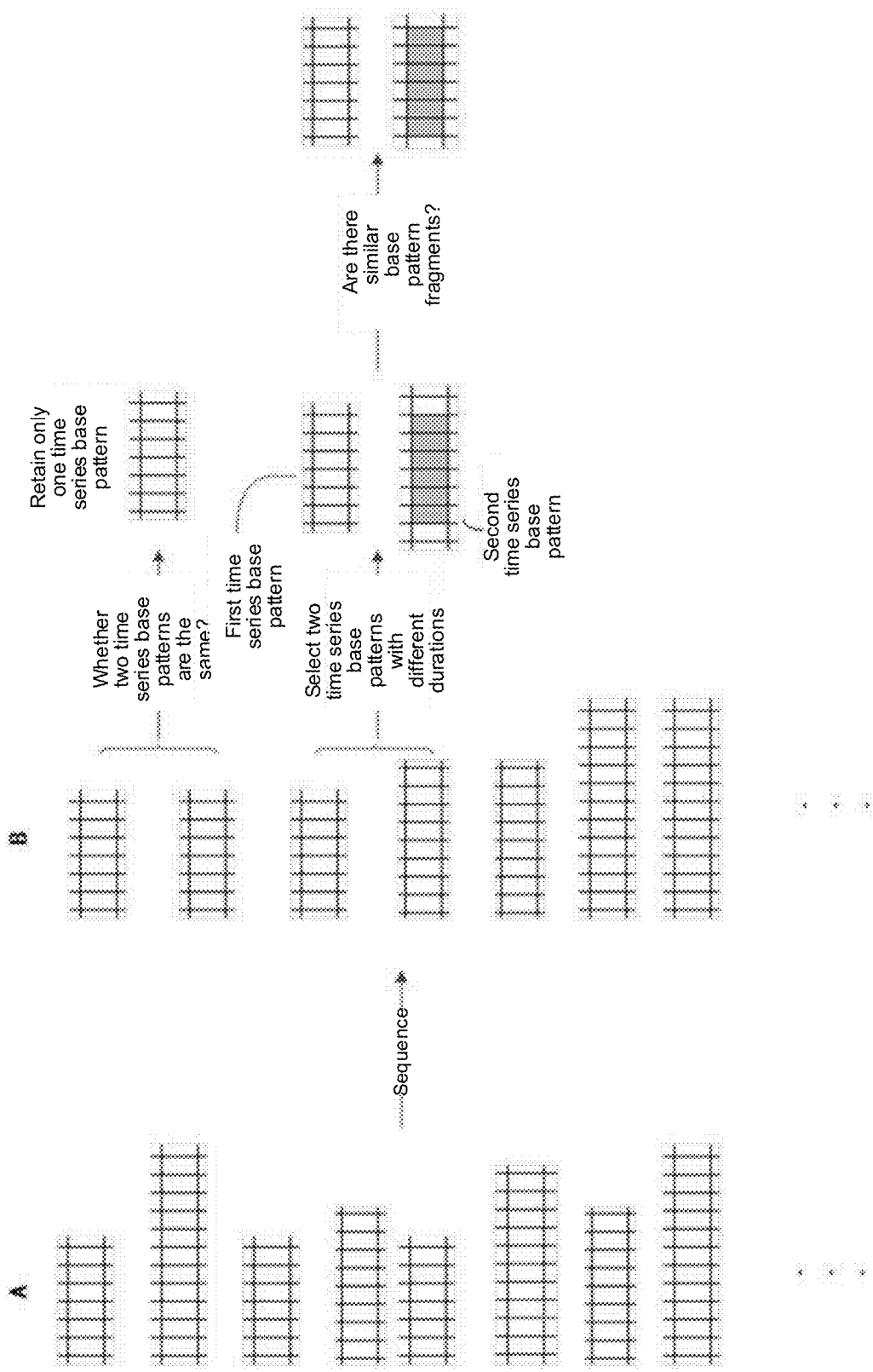
FIG. 3B is a structural diagram showing a process of another method for processing time series data, in accordance with some embodiments.

Optionally, referring to FIGS. 3A and 3B, the method for processing the time series data further includes S301 to S302.

In S301, time series base patterns with different durations in the time series base pattern library are sequenced according to durations of the time series base patterns.

In S302, time series base patterns with the same duration in the time series base pattern library are sequenced according to values of the time series base patterns.

The time series data is a kind of data that changes depending on time and reflects a degree of change through values. Therefore, the time series data have two key indexes, i.e., a monitoring duration and a monitoring value. Since the time series base pattern is a data fragment obtained by dividing the time series data, the time series base pattern also has two indexes, i.e., the duration and the value, which are the same as the time series data. The time series base patterns in the time series base pattern library may be sequenced according to the two indexes of the time series base pattern.

In FIG. 3B, it is assumed that a time series base pattern library A has been constructed after the S203. In this case, the time series base patterns in the time series base pattern library A are arranged out of order. In order to use the time series base pattern library A more conveniently, the time series base patterns in the time series base pattern library A may be arranged in a lexicographic order. The lexicographic order refers to arranging the time series base pattern with a shorter duration before the time series base pattern with a longer duration, and arranging the time series base pattern with a smaller value before the time series base pattern with a larger value. For example, it is assumed that the time series base pattern library is a time series base pattern library A {"3454", "44", "11", "779", "132", "12"}, and a time series base pattern library B formed after sequencing the time base pattern library A is {"11", "12", "44", "132", "779", "3454"}. Herein, taking the time series base pattern "3454" as an example, the number of digits indicates the duration of the time series base pattern, and the magnitude indicates the value of the time series base pattern. Through this sequencing manner, the time series base patterns with short duration may be arranged in front positions, and the time series base patterns with high similarity may be arranged at positions close to each other, which is convenient to add the base pattern identifier to the time series base pattern. After sequencing, the time series base pattern library B may be obtained. The time series base pattern library B may facilitate identification of specific time series fragments in the time series data.

Optionally, referring to FIG. 3A, the method for processing the time series data further includes S303 to S307, which can be used to denoise the time series base pattern library.

In S303, a first time series base pattern and a second time series base pattern are selected from the time series base pattern library. A duration of the first time series base pattern is less than a duration of the second time series base pattern.

In S304, a target base pattern fragment is obtained from the second time series base pattern.

In S305, it is determined whether a similarity between the target base pattern fragment and the first time series base pattern is greater than or equal to a first similarity threshold.

In S306, the second time series base pattern in the time series base pattern library is updated to the target base pattern fragment in response to determining that the similarity between the target base pattern fragment and the first time series base pattern is greater than or equal to the first similarity threshold.

In S307, the second time series base pattern is not updated in response to determining that the similarity between the target base pattern fragment and the first time series base pattern is less than the first similarity threshold.

In general, the time series data include noise. Therefore, the time series base patterns obtained based on the time series data also include noise. The time series base pattern with a longer duration (the time series base pattern including more data) is likely include more noise than the time series base pattern with a shorter duration. For example, in FIG. 3B, it is assumed that the sequenced time series base pattern library B (or the unsequenced time series base pattern library A) includes a first time series base pattern with a shorter duration and a second time series base pattern with a longer duration. The second time series base pattern includes a time series fragment (e.g., a gray target base pattern fragment in the second time series base pattern) similar to the first time series base pattern. Such the first time series base pattern and the second time series base pattern may both be added with the same base pattern identifier. In such a case, the base pattern identifier may be added to the second time series base pattern only through the gray fragments in the second time series base pattern, without requiring the data of white fragments. Accordingly, the white fragments in the second time series base pattern may be regarded as noise, and the second time series base pattern may be replaced with the gray target base pattern fragments to achieve a purpose of denoising the second time series base pattern.

Of course, if the second time series base pattern does not include a data fragment similar to the first time series base pattern, the second time series base pattern may not be updated. In this case, a third time series base pattern may be selected from the time series base pattern library. A duration of the third time series base pattern is less than the duration of the second time series base pattern. Then, the third time series base pattern may be similarly compared with the second time series base pattern to determine whether the second time series base pattern includes a data fragment similar to the third time series base pattern. In a case where all the time series base patterns with durations less than the duration of the second time series base pattern are not similar to the second time series base pattern, it may be determined that the noise in the second time series base pattern is little, and the second time series base pattern may no longer be denoised.

In some embodiments, the similarity between the target base pattern fragment and the first time series base pattern is measured by using any of the above similarity functions. Of course, the similarity between the target base pattern fragment and the first time series base pattern may also be an average value of the similarities calculated by a plurality of functions in the above similarity functions.

In the S303 to S307, the time series base pattern with a longer duration is replaced with the time series base pattern with a shorter duration, thereby reducing noise in the time series base pattern with the longer duration. In addition, a overall size of the time series base pattern library may be reduced, and the time series base pattern library may be compressed.

Compared with the unsequenced time series base pattern library A, an efficiency of performing the S303 to S307 in the sequenced time series base pattern library B is higher. Since it is possible to always use a time series base pattern at a top sequence as the first time series base pattern, and compare the time series base patterns with a time series base pattern at a bottom sequence. Therefore, when the fragment (noise) that is not similar to the first time series base pattern has been removed from the second time series base pattern, other time series base patterns with durations less than the duration of the second time series base pattern will no longer be used to be compared with the second time series base pattern, which may improve an efficiency of the whole compression and denoising process.

Optionally, referring to FIGS. 3A and 3B, the method for processing the time series data further includes S308.

In S308, in a case where there is a repeated time series base pattern, the repeated time series base pattern is deleted.

For example, after the second time series base pattern is updated to the target base pattern fragment, in a case where there are a plurality of time series base patterns that are the same to each other, a time series base pattern at the top sequence is retained, and the remaining time series base patterns at the bottom sequence are deleted.

By deleting the repeated time series base pattern, it is possible to further compress the size of the time series base pattern library, so as to avoid using repeated time series base pattern to identify specific time series fragments, thereby improving an efficiency of identifying specific time series fragments.

The method for processing the time series data in some embodiments of the present disclosure further includes: identifying specific time series fragments in the time series data to be identified by using the time series base pattern library constructed with the time series data.

Figure 4A:
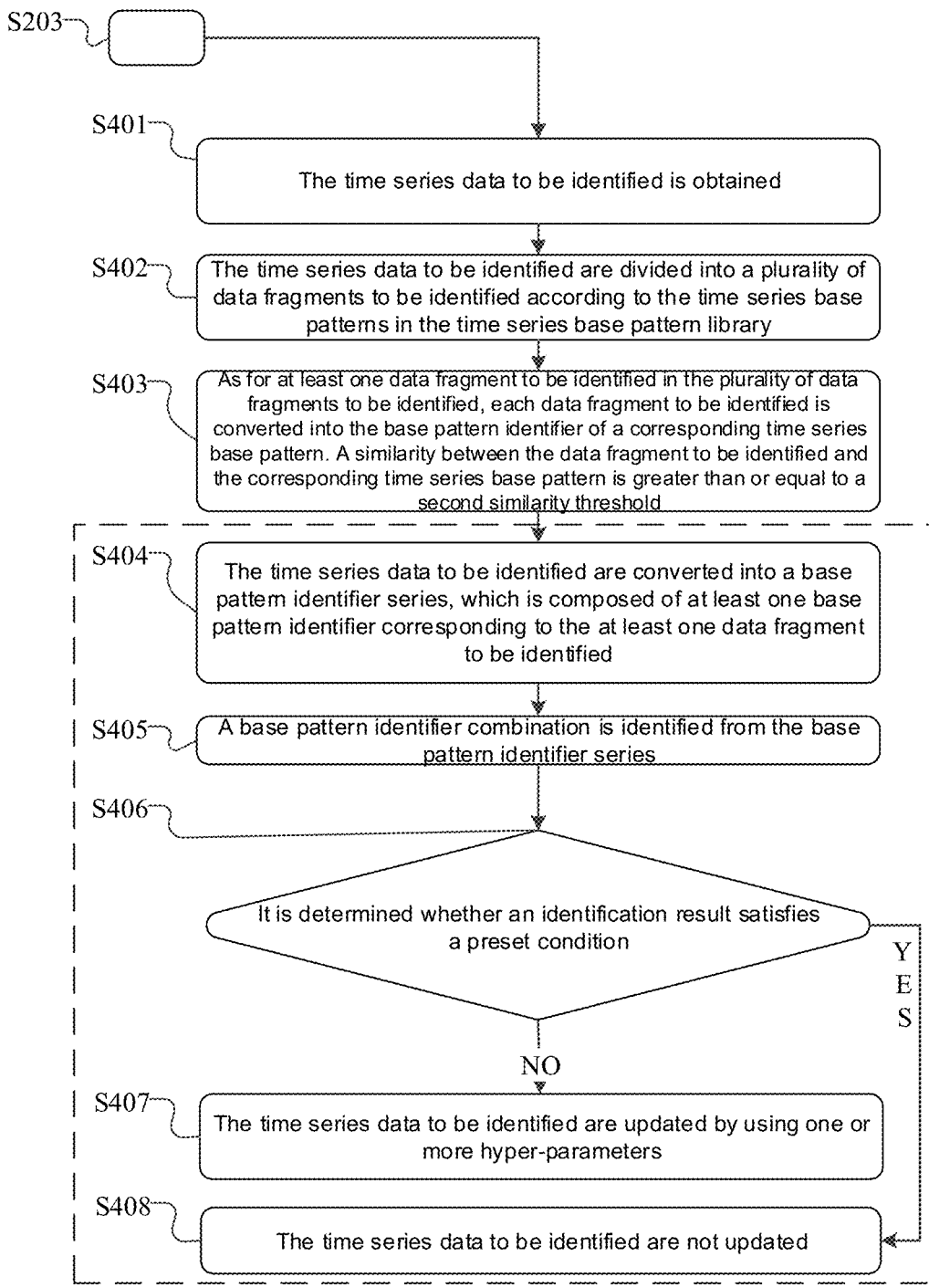
FIG. 4A is a flow diagram of yet another method for processing time series data, in accordance with some embodiments.
Figure 4B:
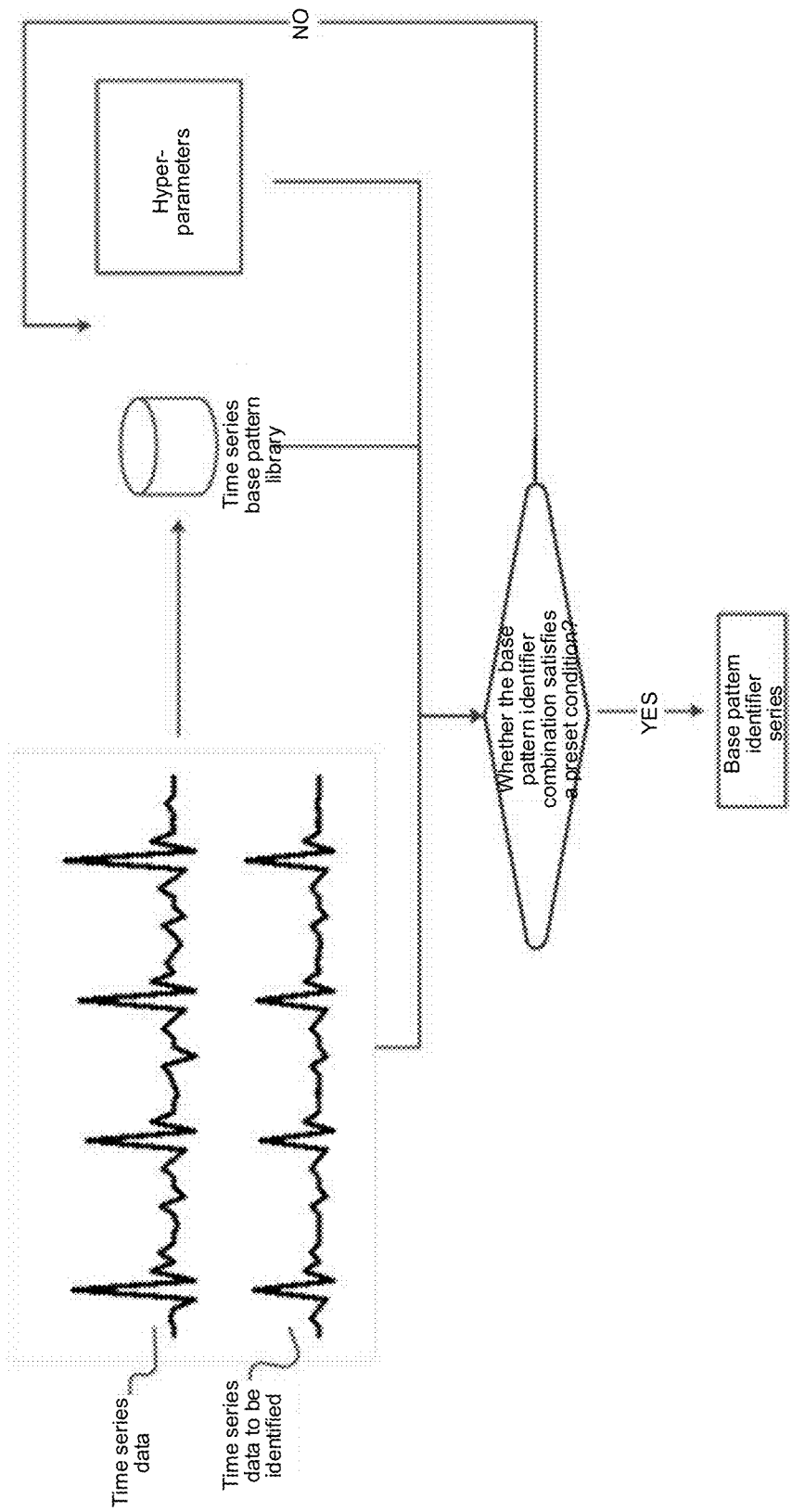
FIG. 4B is a flow diagram of yet another method for processing time series data, in accordance with some embodiments.
Figure 4C:
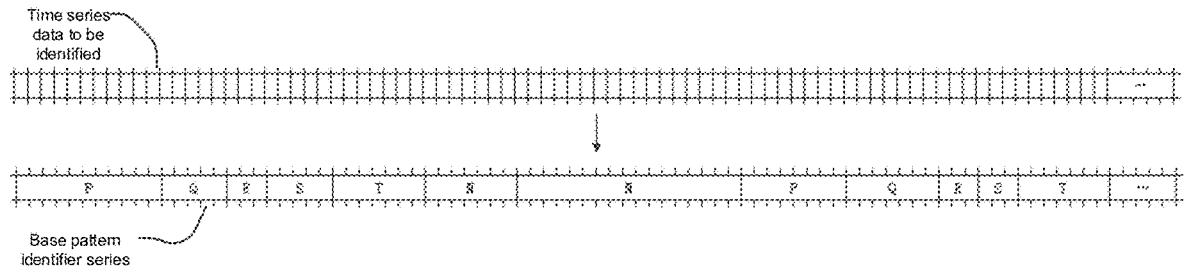
FIG. 4C is a structural diagram showing a process of yet another method for processing time series data, in accordance with some embodiments.

In some examples, referring to FIGS. 4A, 4B and 4C, the method for processing the time series data further includes S401 to S403.

In S401, the time series data to be identified is obtained.

FIG. 4B exemplarily shows the time series data and the time series data to be identified. The statistical characteristics and changing trends of both the time series data and the time series data to be identified are generally similar. Therefore, the time series base pattern library may be used to identify specific time series fragments of the time series data to be identified.

In S402, the time series data to be identified are divided into a plurality of data fragments to be identified according to the time series base patterns in the time series base pattern library.

In S403, as for at least one data fragment to be identified in the plurality of data fragments to be identified, each data fragment to be identified is converted into the base pattern identifier of a corresponding time series base pattern. A similarity between the data fragment to be identified and the corresponding time series base pattern is greater than or equal to a second similarity threshold.

In the at least one data fragment to be identified, any data fragment to be identified corresponds to one time series base pattern. That is, the similarity between the data fragment to be identified and the time series base pattern is greater than or equal to the second similarity threshold.

For example, at least one time series base pattern in the time series base pattern library is selected according to a duration sequence of the time series base patterns and/or a value sequence of the time series base patterns. And the time series data to be identified are divided into the data fragments to be identified according to the at least one selected time series base pattern.

For example, it is assumed that the time series base pattern library is the time series base pattern library B sequenced in the lexicographic order. Then, the time series base patterns are selected one by one according to the sequencing manner of the time series base patterns in the time series base pattern library B to compare with the time series data to be identified. It is assumed that the time series data to be identified include 1000 frames of data, a shortest time series base pattern in the time series base pattern library B is 30 frames, and a next shortest time series base pattern is 35 frames. Then, a first 30 frames of data of the time series data to be identified may be used as a data fragment to be identified, and the data fragment to be identified is compared with the time series base patterns with a duration of 30 frames one by one. If a time series base pattern, a similarity between which and the data fragment to be identified is greater than or equal to the second similarity threshold, is found, the data fragment to be identified will be converted into a base pattern identifier corresponding to the time series base pattern, and the data fragment to be identified is an identifiable data fragment. Then remaining 970 frames of data are continued to be divided until all the data fragments to be identified in the time series data to be identified have been converted. If a time series base pattern, the similarity between which and the data fragment to be identified is greater than or equal to the second similarity threshold, and with a duration of 30 frames, is not found, a first 35 frames of data of the time series data to be identified can be used as the data fragment to be identified, and then the data fragment to be identified is compared with time series base patterns with a duration of 35 frames in the time series base pattern library. The steps are repeated until the traversal of the entire time series base pattern library is completed. FIG. 4C shows an example in which the time series data to be identified are converted into a base pattern identifier series.

It is assumed that the entire time series base pattern library B is traversed, and the time series base pattern, the similarity between which and the data fragment to be identified is greater than or equal to the second similarity threshold, cannot be found, a first frame of data currently unidentified can be discarded, and data starting from a second frame of data can be re-divided into the data fragment to be identified until the time series base pattern, the similarity between which and the data fragment to be identified is greater than or equal to the second similarity threshold, is found.

In some examples, referring to FIG. 4A, the method for processing the time series data further includes S404 to S408.

In S404, the time series data to be identified are converted into a base pattern identifier series, which is composed of at least one base pattern identifier corresponding to the at least one data fragment to be identified.

After the S401 to S403, the time series data to be identified are divided into the plurality of data fragments to be identified, and after being compared with the time series base pattern library, all or part of the data fragments to be identified in the plurality of data fragments to be identified are converted into base pattern identifiers. These base pattern identifiers form a base pattern identifier series according to a time series sequence, and the time series data to be identified are converted into the corresponding base pattern identifier series. For example, the ECG data are converted into a base pattern identifier series of "PQRSTNNPQRST . . . " (N identifier indicates data when the heart is not contracted). As mentioned above, the specific time series fragment in the ECG data is a combination of "QRS" identifiers. Therefore, it makes sense to identify a specific base pattern identifier combination in the base pattern identifier series.

The base pattern identifier combination is formed by combining some base pattern identifiers. For example, the base pattern identifier combination is a plurality of base pattern identifiers arranged in a specific order (e.g., the base pattern identifier combination of the "QRS" in the ECG data). The base pattern identifier combination may also include a certain number of certain base pattern identifiers. For example, there are three identical base pattern identifiers in five consecutive base pattern identifiers.

It will be seen from the above that the specific base pattern identifier combination may represent a specific time series fragment. For example, in the ECG data, a time series fragment composed of Q wave, R wave and S wave generally represents a moment when the heart contracts. Therefore, if the base pattern identifier series includes enough base pattern identifier combinations, i.e., combinations of the "Q wave to R wave to S wave", it may be determined that the specific time series fragment in the time series data to be identified has been successfully identified.

In S405, a base pattern identifier combination is identified from the base pattern identifier series.

In S406, it is determined whether an identification result satisfies a preset condition.

In S407, the time series data to be identified are updated by using one or more hyper-parameters in response to determining that the identification result satisfies the preset condition.

In S408, the time series data to be identified are not updated in response to determining that the identification result does not satisfy the preset condition.

Since the time series data to be identified and the time series data are generally acquired for different objects under different conditions, there may be a difference in the overall characteristics of data between the time series data to be identified and the time series data. For example, as shown in FIG. 4B, amplitude values of the time series data to be identified are smaller than amplitude values of the time series data as a whole. It is assumed that the time series data and the time series data to be identified in FIG. 4B are all ECG data. A fluctuation interval of peak-to-valley values of the time series data is 10, and a time series base pattern library is constructed based on such time series data. A fluctuation interval of peak-to-valley values of the time series data to be identified is 2, and the time series data to be identified include a plurality of heartbeats. In this case, directly using the time series base pattern library may still identify the heartbeat part of the time series data to be identified as noise, or identify the R wave in the heartbeat as P wave, and thus only a small number of heartbeats among the plurality of heartbeats may be identified. For example, it is assumed that the time series data to be identified with the fluctuation interval of the peak-to-valley values being 2 should be converted into a base pattern identifier series "PQRSTNNNNPQRSTNNN" (including two "QRS" identifier combinations). If the time series data with the fluctuation interval of the peak-to-valley values being 10 are used to construct the time series base pattern library, the time series data to be identified may be converted into a base pattern identifier series "NNPNNNNNNPNNNNNN" (not including the "QRS" identifier combination). The base pattern identifier series that is converted in this way does not include enough "QRS" identifiers.

Based on this, in order to make the time series base pattern library well match the time series data to be identified, the time series data to be identified needs to be preprocessed.

That is, the time series data to be identified are updated by using one or more hyper-parameters to achieve better results.

In some examples, the preset condition is that a sufficient number of specific time series fragments are not identified. In some other examples, the preset condition is that the identified specific time series fragment is not accurate enough. The embodiments of the present disclosure do not limit the preset condition, as long as a good identification effect of the specific time series fragment of the time series data to be identified can be obtained.

The ECG data is taken as an example again. In the field of ECG data analysis, there are two hyper-parameters that have a great influence on the ECG data analysis: an energy threshold T and an interval period R between an R wave and another R wave. The two hyper-parameters can be used to update the time series data to be identified. FIG. 4B is taken as an example, since an overall amplitude value of the time series data to be identified is smaller than an overall amplitude value of the time series data, the amplitude value of the time series data to be identified needs to be adjusted. A raw T and a raw R can be used to adjust the time series data to be identified. For example, it is assumed that a maximum value of the amplitude values in the time series data to be identified is MAX. Then, a data value (i.e., an amplitude value) K of each frame in the time series data to be identified may be adjusted to K1, which is a quotient of a product of K and T and MAX (K1=K×T/MAX). Therefore, it may be ensured that the data value of each frame in the time series data to be identified does not exceed a raw threshold T. Then, the adjusted time series data to be identified can be identified again. If enough base pattern identifier combinations cannot be still obtained, the raw T may be adjusted. For example, the raw T is adjusted to T1, which is a product of T and C (T1=T×C), by using a shrinkage coefficient C. Then the data value K of each frame in the time series data to be identified is adjusted to K2, which is a quotient of a product of K and T1 and MAX (K2=K×T1/MAX). The steps are repeated until enough base pattern identifier combinations are obtained.

The following shows an example algorithm to detect QRS waveband in the ECG data.

---
Algorithm 1 Recursive QRS Detector
---
1: Input: Raw ECG recording X, parameters shrink coefficient c
2: Output: QRS indexes Q
3: Initialize: Energy threshold of the detector T, refractory period in second between two R-peaks R
4: while stopping condition not satisfied do
5:    T = c * T
6:    R = c * R
7:    Q = BasicQRSDetector(X, T, R)
8: end while
---

An input in the algorithm is the time series data to be identified—a raw ECG recording X and the shrinkage coefficient C. An output of the algorithm is a starting band of a QRS waveband—an index of a Q wave. A function to obtain the index of the Q wave is BasicQRSDetector(X, T, R). In the BasicQRSDetector(X, T, R) function, the raw ECG recording X is compared with the time series base pattern library after being adjusted by T and R, so as to obtain an index position of the Q wave in the QRS waveband. In this way, segmentation and identification of the specific time series fragment, i.e., the QRS waveband, in the raw ECG recording X is realized.

By using the shrinkage coefficient, the method for processing the time series data according to the embodiments of the present disclosure does not need to fix the hyper-parameters of a model, but recursively update the values of the hyper-parameters again and again, so as to adjust the time series data to be identified to a state where enough specific time series fragments can be identified, thereby eliminating most of the influences caused by different sampling conditions and different sampling objects of the device, and further improving accuracy of identifying specific time series fragments.

Figure 5:
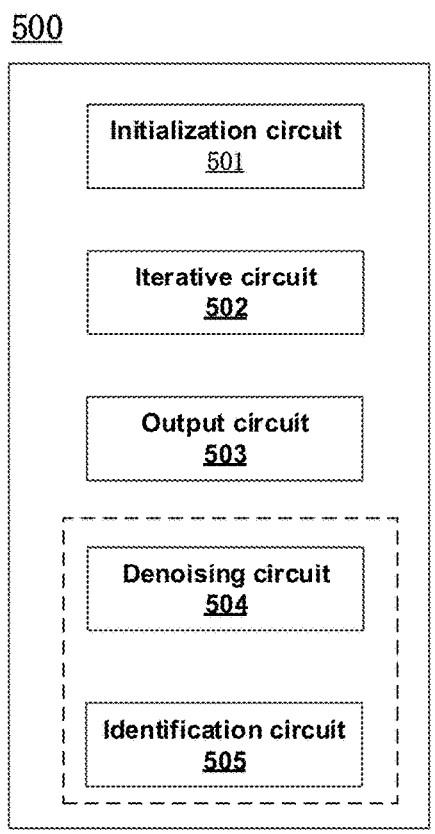
FIG. 5 is a structural diagram of an apparatus for processing time series data, in accordance with some embodiments.

As shown in FIG. 5, an apparatus 500 for processing time series data includes an initialization circuit 501, an iterative circuit 502 and an output circuit 503.

The initialization circuit 501 is configured to divide time series data into a plurality of data fragments according to an objective function, and the objective function enables the plurality of data fragments to have a greatest similarity.

The iterative circuit 502 is configured to, in response to determining that at least one data fragment in the plurality of data fragments does not satisfy an iteration termination condition, perform following iterative operations on the at least one data fragment. The iterative operations include: using the at least one data fragment as at least one update time series fragment; dividing each update time series fragment into a plurality of update data fragments according to the objective function; using each update data fragment that does not satisfy the iteration termination condition in the plurality of update data fragments as a new update time series fragment, so as to continue to divide the new update time series fragment according to the objective function; and using each update data fragment that satisfies the iteration termination condition in the plurality of update data fragments as a time series base pattern.

The output circuit 503 is configured to construct a time series base pattern library by using the time series base patterns, and the time series base pattern library includes a plurality of time series base patterns.

For example, the initialization circuit 501, iterative circuit 502 and the output circuit 503 may be implemented by a processor that executes computer instructions, or may be implemented by a circuit. For example, the initialization circuit 501, the iterative circuit 502 and the output circuit 503 may be one or more physical blocks or logical blocks including computer instructions. For example, the computer instructions may be constructed as objects, procedures or functions. Nevertheless, the computer instructions in the initialization circuit 501, the iterative circuit 502 and the output circuit 503 do not need to be physically located together, but may include different computer instructions stored on different physical blocks. Those skilled in the art can build hardware circuits corresponding to the above computer instructions to implement corresponding functions. The hardware circuits include conventional very large-scale integration (VLSI) circuits or gate arrays, and existing semiconductors such as logic chips and transistors, or other discrete components. The circuits may also be implemented by programmable hardware devices, such as field programmable gate arrays, programmable array logic, programmable logic devices.

Optionally, the apparatus 500 for processing the time series data further includes a denoising circuit 504. The denoising circuit 504 is configured to perform following denoising operations. The denoising operations include: selecting a first time series base pattern and a second time series base pattern from the time series base pattern library, a duration of the first time series base pattern being less than a duration of the second time series base pattern; obtaining a target base pattern fragment from the second time series base pattern; determining whether a similarity between the target base pattern fragment and the first time series base pattern is greater than or equal to a first similarity threshold; updating the second time series base pattern to the target base pattern fragment if the similarity between the target base pattern fragment and the first time series base pattern is greater than or equal to the first similarity threshold; not updating the second time series base pattern if the similarity between the target base pattern fragment and the first time series base pattern is less than the first similarity threshold.

Optionally, the apparatus 500 for processing the time series data further includes an identification circuit 505, and the identification circuit 505 is configured to add a base pattern identifier to each time series base pattern in the time series base pattern library.

Figure 6:
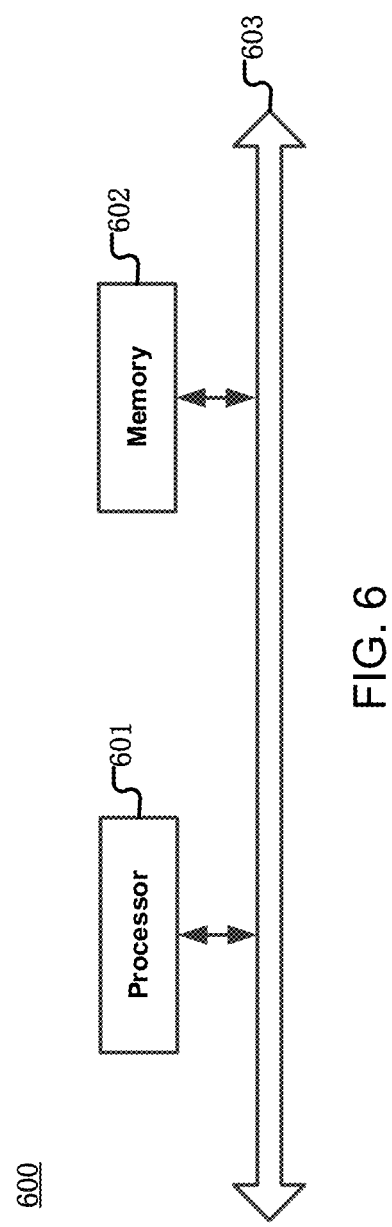
FIG. 6 is a structural diagram of an electronic device for processing time series data, in accordance with some embodiments.

In some embodiments, referring to FIG. 6, an electronic device 600 for processing time series data is provided. The electronic device 600 includes a processor 601 and a memory 602. The processor 601 and the memory 602 may be connected through a bus 603.

The processor 601 can perform various actions and processing according to a program stored in the memory 602. The processor 601 may be an integrated circuit chip with signal processing capability. The processor may be a general-purpose processor, a digital signal processor (DSP), an application specific integrated circuit (ASIC), a field programmable gate array (FPGA) or other programmable logic devices, discrete gate or transistor logic devices, or discrete hardware components, which can implement or execute various methods, steps and logical block diagrams disclosed in the embodiments of the present disclosure. The general-purpose processor may be a microprocessor, or the processor may also be any conventional processor, and may be of an X86 architecture or an ARM architecture.

The memory 602 has stored therein computer instructions that, when executed by the processor 601, cause the processor to implement the method for processing the time series data. The memory 602 may be volatile memory or non-volatile memory, or may include both volatile and non-volatile memory. The non-volatile memory may be read only memory (ROM), programmable read only memory (PROM), erasable programmable read only memory (EPROM), electrically erasable programmable read only memory (EEPROM) or flash memory. The volatile memory may be random access memory (RAM), which acts as an external cache. By way of exemplary but not restrictive description, many forms of RAM are available, such as static random access memory (SRAM), dynamic random access memory (DRAM), synchronous dynamic random access memory (SDRAM), double data rate synchronous dynamic random access memory (DDRSDRAM), enhanced synchronous dynamic random access memory (ESDRAM), synchronous link dynamic random access memory (SLDRAM), and direct rambus random access memory (DRRAM). It will be noted that the memory described herein is intended to include, but is not limited to, these and any other suitable type of memory.

Some embodiments of the present disclosure provide a non-transitory computer-readable storage medium. The computer-readable storage medium has stored thereon computer program instructions that, when run on a processor, cause the processor to execute one or more steps in the method as described in any one of the above embodiments.

For example, the computer-readable storage medium may include, but is not limited to a magnetic storage device (such as a hard disk, a floppy disk or a magnetic tape), an optical disk (such as a compact disk (CD), a digital versatile disk (DVD)), a smart card or a flash memory device (e.g., an erasable programmable read-only memory (EPROM), a card, a stick or a key driver). Various computer-readable storage media described in the present disclosure may represent one or more devices and/or other machine-readable storage media for storing information. The term "machine-readable storage media" may include, but are not limited to, wireless channels and various other media capable of storing, containing and/or carrying instructions and/or data.

Some embodiments of the present disclosure provide a computer program product. The computer program product includes computer program instructions that, when executed on a computer, cause the computer to execute one or more steps in the method as described in the above embodiments.

Some embodiments of the present disclosure provide a computer program. When the computer program is executed on a computer, the computer program causes the computer to execute one or more steps in the method as described in the above embodiments.

Beneficial effects of the above computer-readable storage medium, computer program product, and computer program are the same as the beneficial effects of the method as described in some of the above embodiments, which will not be repeated herein.

The method, the apparatus and the computer-readable storage medium based on the time series data in the embodiments of the present disclosure may solve the problem that the current time series data analysis technology cannot achieve good analysis effects when facing time series data with highly complex noise and severe data skew, thereby improving the accuracy of processing the time series data.

The foregoing descriptions are merely specific implementations of the present disclosure, but the protection scope of the present disclosure is not limited thereto. Changes or replacements that any person skilled in the art could conceive of within the technical scope of the present disclosure shall all be included in the protection scope of the present disclosure. Therefore, the protection scope of the present disclosure shall be subject to the protection scope of the claims.

What is claimed is:

1. A method for processing time series data applied to an electronic device, the electronic device comprising a processor and a memory, the method comprising:
   dividing, by the processor, time series data into a plurality of data fragments according to an objective function, wherein the plurality of data fragments have a greatest similarity, and number of the plurality of data fragments is determined according to computing resources of the electronic device;
   in response to determining that at least one data fragment in the plurality of data fragments does not satisfy an iteration termination condition, performing, by the processor, following iterative operations on the at least one data fragment:
     using the at least one data fragment as at least one update time series fragment;
     dividing each update time series fragment into a plurality of update data fragments according to the objective function;
     using each update data fragment that does not satisfy the iteration termination condition in the plurality of update data fragments as a new update time series fragment, so as to continue to divide the new update time series fragment according to the objective function; and using each update data fragment that satisfies the iteration termination condition in the plurality of update data fragments as a time series base pattern; and constructing, by the processor, a time series base pattern library by using a plurality of time series base patterns such that the time series base pattern library includes the plurality of time series base patterns, wherein the plurality of time series base patterns is used to identify time series data to be identified that have similar characteristics to the time series data.

2. The method according to claim 1, wherein before constructing, by the processor, the time series base pattern library, the method further comprises:

using, by the processor, any one of the plurality of data fragments that satisfies the iteration termination condition as another time series base pattern.

3. The method according to claim 1, wherein the iteration termination condition is a duration threshold condition.

4. The method according to claim 1, wherein constructing, by the processor, the time series base pattern library by using the plurality of time series base patterns, includes:

as for each time series base pattern, determining, by the processor, whether a same time series base pattern exists in the time series base pattern library;

discarding, by the processor, the time series base pattern in response to determining that the same time series base pattern exists in the time series base pattern library; and adding, by the processor, the time series base pattern to the time series base pattern library in response to determining that the same time series base pattern does not exist in the time series base pattern library.

5. The method according to claim 1, wherein constructing, by the processor, the time series base pattern library by using the plurality of time series base patterns, includes:

adding, by the processor, the plurality of time series base patterns to the time series base pattern library; and deleting, by the processor, a repeated time series base pattern in the time series base pattern library.

6. The method according to claim 1, further comprising:

sequencing, by the processor, time series base patterns with different durations in the time series base pattern library according to durations of the time series base patterns; and sequencing, by the processor, time series base patterns with a same duration in the time series base pattern library according to values of the time series base patterns.

7. The method according to claim 1, further comprising:

selecting, by the processor, a first time series base pattern and a second time series base pattern from the time series base pattern library, wherein a duration of the first time series base pattern is less than a duration of the second time series base pattern;

obtaining, by the processor, a target base pattern fragment from the second time series base pattern;

determining, by the processor, whether a similarity between the target base pattern fragment and the first time series base pattern is greater than or equal to a first similarity threshold;

updating, by the processor, the second time series base pattern to the target base pattern fragment in response to determining that the similarity between the target base pattern fragment and the first time series base pattern is greater than or equal to the first similarity threshold; and not updating, by the processor, the second time series base pattern in response to determining that the similarity between the target base pattern fragment and the first time series base pattern is less than the first similarity threshold.

8. The method according to claim 7, further comprising:

deleting, by the processor, a repeated time series base pattern in the time series base pattern library.

9. The method according to claim 1, further comprising:

adding, by the processor, a base pattern identifier to each time series base pattern in the time series base pattern library.

10. The method according to claim 9, further comprising:

obtaining, by the processor, time series data to be identified;

dividing, by the processor, the time series data to be identified into a plurality of data fragments to be identified according to time series base patterns in the time series base pattern library; and as for at least one of the plurality of data fragments to be identified, converting, by the processor, each data fragment to be identified into the base pattern identifier of a corresponding time series base pattern, wherein a similarity between the data fragment to be identified and the corresponding time series base pattern is greater than or equal to a second similarity threshold.

11. The method according to claim 10, wherein dividing, by the processor, the time series data to be identified into the plurality of data fragments to be identified according to the time series base patterns in the time series base pattern library, includes:

selecting, by the processor, at least one time series base pattern in the time series base pattern library according to a duration sequence of the time series base patterns and/or a value sequence of the time series base patterns; and dividing, by the processor, the time series data to be identified into the data fragments to be identified according to the at least one selected time series base pattern.

12. The method according to claim 11, wherein dividing, by the processor, the time series data to be identified into the data fragments to be identified according to the at least one selected time series base pattern, includes:

dividing, by the processor, the time series data to be identified into at least one data fragment to be identified according to a selected time series base pattern;

determining, by the processor, whether a similarity between any one of the at least one data fragment to be identified and the selected time series base pattern is less than the second similarity threshold; and selecting, by the processor, a next time series base pattern in the time series base pattern library to divide remaining time series data to be identified according to the duration sequence of the time series base patterns and/or the value sequence of the time series base patterns, in response to determining that the similarity between any one of the at least one data fragment to be identified and the selected time series base pattern is less than the second similarity threshold; and converting, by the processor, the each data fragment to be identified into the base pattern identifier of the corresponding time series base pattern, includes: converting the data fragment to be identified into a base pattern identifier corresponding to the selected time series base pattern, in response to determining that the similarity between any one of the at least one data fragment to be identified and the selected time series base pattern is greater than or equal to the second similarity threshold.

13. The method according to claim 12, wherein dividing, by the processor, the time series data to be identified into the data fragments to be identified according to the at least one selected time series base pattern, further includes:
discarding, by the processor, a first frame of data in the time series data to be identified if the similarity between any data fragment to be identified and a corresponding time series base pattern is less than the second similarity threshold when the time series data to be identified are divided into at least one data fragment to be identified according to any time series base pattern in the time series base pattern library; and
using, by the processor, remaining data of the time series data to be identified as new time series data to be identified.

14. The method according to claim 10, further comprising:
converting, by the processor, the time series data to be identified into a base pattern identifier series, the base pattern identifier series being composed of at least one base pattern identifier corresponding to the at least one data fragment to be identified;
identifying, by the processor, a base pattern identifier combination from the base pattern identifier series;
determining, by the processor, whether an identification result satisfies a preset condition;
updating, by the processor, the time series data to be identified by using one or more hyper-parameters in response to determining that the identification result satisfies the preset condition; and
not updating, by the processor, the time series data to be identified in response to determining that the identification result does not satisfy the preset condition.

15. The method according to claim 1, wherein the similarity is calculated by a similarity function, and the similarity function is any one of following functions:
cosine similarity calculation function, Euclidean distance calculation function, Manhattan distance calculation function, Minkowski distance calculation function or Pearson correlation coefficient calculation function.

16. An apparatus for processing time series data applied to an electronic device, the apparatus comprising:
an initialization circuit configured to divide time series data into a plurality of data fragments according to an objective function, wherein the objective function enables the plurality of data fragments to have a greatest similarity, and number of the plurality of data fragments is determined according to computing resources of the electronic device;
an iterative circuit configured to in response to determining that at least one data fragment in the plurality of data fragments does not satisfy an iteration termination condition, perform following iterative operations on the at least one data fragment;
using the at least one data fragment as at least one update time series fragment;
dividing each update time series fragment into a plurality of update data fragments according to the objective function;
using each update data fragment that does not satisfy the iteration termination condition in the plurality of update data fragments as a new update time series fragment, so as to continue to divide the new update time series fragment according to the objective function; and
using each update data fragment that satisfies the iteration termination condition in the plurality of update data fragments as a time series base pattern; and
an output circuit configured to construct a time series base pattern library by using a plurality of time series base patterns such that the time series base pattern library includes the plurality of time series base patterns, wherein the plurality of time series base patterns are used to identify time series data to be identified that have similar characteristics to the time series data.

17. The apparatus according to claim 16, further comprising:
a denoising circuit configured to perform following denoising operations:
selecting a first time series base pattern and a second time series base pattern from the time series base pattern library, wherein a duration of the first time series base pattern is less than a duration of the second time series base pattern;
obtaining a target base pattern fragment from the second time series base pattern;
determining whether a similarity between the target base pattern fragment and the first time series base pattern is greater than or equal to a first similarity threshold;
updating the second time series base pattern to the target base pattern fragment in response to determining that the similarity between the target base pattern fragment and the first time series base pattern is greater than or equal to the first similarity threshold; and
not updating the second time series base pattern in response to determining that the similarity between the target base pattern fragment and the first time series base pattern is less than the first similarity threshold.

18. The apparatus according to claim 16, further comprising:
an identification circuit configured to add a base pattern identifier to each time series base pattern in the time series base pattern library.

19. An electronic device for processing time series data, comprising:
a processor; and
a memory, wherein the memory has stored therein computer instructions that, when executed by the processor, cause the processor to implement a method for processing time series data, and the method comprises:
dividing, by the processor, time series data into a plurality of data fragments according to an objective function, wherein the plurality of data fragments have a greatest similarity, and number of the plurality of data fragments is determined according to computing resources of the electronic device;
in response to determining that at least one data fragment in the plurality of data fragments does not satisfy an iteration termination condition, performing, by the processor, following iterative operations on the at least one data fragment:
using the at least one data fragment as at least one update time series fragment;
dividing each update time series fragment into a plurality of update data fragments according to the objective function;
using each update data fragment that does not satisfy the iteration termination condition in the plurality of update data fragments as a new update time series fragment, so as to continue to divide the new update time series fragment according to the objective function; and using each update data fragment that satisfies the iteration termination condition in the plurality of update data fragments as a time series base pattern; and constructing, by the processor, a time series base pattern library by using a plurality of time series base patterns such that the time series base pattern library includes the plurality of time series base patterns, wherein the plurality of time series base patterns is used to identify time series data to be identified that have similar characteristics to the time series data.

20. A non-transitory computer-readable storage medium, wherein the computer-readable storage medium has stored thereon computer program instructions that, when executed by a processor, cause the processor to implement the method according to claim 1.

* * * * *